US012453576B2

(12) United States Patent
Nishio et al.

(10) Patent No.: US 12,453,576 B2
(45) Date of Patent: Oct. 28, 2025

(54) MEDICAL DEVICE

(71) Applicant: TERUMO KABUSHIKI KAISHA, Tokyo (JP)

(72) Inventors: Kosuke Nishio, Machida (JP); Tomonori Hatta, San Jose, CA (US); Taiga Nakano, Cupertino, CA (US); Junichi Kobayashi, Cupertino, CA (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 916 days.

(21) Appl. No.: 17/118,886

(22) Filed: Dec. 11, 2020

(65) Prior Publication Data

US 2021/0093349 A1 Apr. 1, 2021

Related U.S. Application Data

(63) Continuation of application No. PCT/IB2019/058115, filed on Sep. 25, 2019.

(30) Foreign Application Priority Data

Aug. 2, 2018 (JP) ................................ 2018-146319

(51) Int. Cl.
*A61B 17/3207* (2006.01)
*A61M 25/09* (2006.01)
(Continued)

(52) U.S. Cl.
CPC *A61B 17/320758* (2013.01); *A61B 2217/005* (2013.01); *A61B 2217/007* (2013.01); *A61M 25/09* (2013.01)

(58) Field of Classification Search
CPC ...... A61B 17/320758; A61B 17/32002; A61B 2017/00685; A61B 2017/320032; A61B 2217/005; A61B 2217/007; A61M 25/09
See application file for complete search history.

(56) References Cited

U.S. PATENT DOCUMENTS 5,405,348 A 4/1995 Anspach et al.
6,156,046 A 12/2000 Passafaro et al.
(Continued)

FOREIGN PATENT DOCUMENTS

JP 2001522631 A 11/2001
JP 2004514463 A 5/2004
(Continued)

OTHER PUBLICATIONS

International Search Report (PCT/ISA/210) and translation and Written Opinion (PCT/ISA/237) mailed on Nov. 12, 2019, by the Japanese Patent Office as the International Searching Authority for International Application No. PCT/IB2019/058115.
(Continued)

*Primary Examiner* — Tan-Uyen T Ho
*Assistant Examiner* — Lindsey R. Rivers
(74) *Attorney, Agent, or Firm* — Buchanan Ingersoll & Rooney PC

(57) ABSTRACT

A medical device is disclosed which can be inserted into a biological lumen to effectively cut and remove an object. The medical device includes a drive shaft, a cutting portion fixed to a distal portion of the drive shaft, an outer tube that accommodates the drive shaft, and a handle unit disposed in a proximal portion of the drive shaft and the outer tube. The handle unit has an aspiration port. The aspiration port communicates with an aspiration lumen disposed between the outer tube and the drive shaft. The drive shaft has a first wire rod helically wound around an axis of the drive shaft. A helical winding direction of the first wire rod wound toward a proximal end direction of the drive shaft is a reverse direction of a rotation direction of the drive shaft. The first wire rod directly faces an inner peripheral surface of the outer tube.

14 Claims, 7 Drawing Sheets

(51) Int. Cl.
*A61B 17/00* (2006.01)
*A61B 17/32* (2006.01)

(56) References Cited

U.S. PATENT DOCUMENTS

| | | | |
|---|---|---|---|
| 9,492,192 B2 | 11/2016 | To et al. | |
| 2002/0007190 A1 | 1/2002 | Wulfman et al. | |
| 2004/0006358 A1* | 1/2004 | Wulfman ....... | A61B 17/320725 606/167 |
| 2008/0033423 A1 | 2/2008 | Peacock | |
| 2011/0118660 A1* | 5/2011 | Torrance ........ | A61B 17/320758 604/35 |
| 2012/0109171 A1 | 5/2012 | Zeroni et al. | |
| 2013/0096587 A1 | 4/2013 | Smith et al. | |

FOREIGN PATENT DOCUMENTS

| | | | |
|---|---|---|---|
| JP | 2008532576 | A | 8/2008 |
| JP | 2014501552 | A | 1/2014 |
| JP | 2014533147 | A | 12/2014 |
| WO | 9923958 | A1 | 5/1999 |

OTHER PUBLICATIONS

English Translations of the International Search Report (Form PCT/ISA/210) and the Written Opinion of the International Searching Authority (Form PCT/ISA/237) issued on Nov. 12, 2019, by the Japanese Patent Office in corresponding International Application No. PCT/IB2019/0058115. (11 pages).

* cited by examiner

MEDICAL DEVICE

CROSS-REFERENCES TO RELATED APPLICATIONS

This application is a continuation of International Application No. PCT/162019/058115 filed on Sep. 25, 2019, which claims priority to Japanese Patent Application No. 2018-146319 filed on Aug. 2, 2018, the entire content of both of which is incorporated herein by reference.

FIELD OF THE INVENTION

The present disclosure generally relates to a medical device for removing an object in a biological lumen, and a method for cutting and aspirating a lesion area inside a blood vessel.

BACKGROUND DISCUSSION

Methods for treating a stenosed site caused by a thrombus, a plaque, or a calcified lesion inside a blood vessel include widening the blood vessel with a balloon and causing a mesh-shaped or coil-shaped stent to indwell the blood vessel as a support for the blood vessel. However, according to these methods, it can be difficult to treat the stenosed site hardened by calcification or the stenosed site appearing in a bifurcated portion of the blood vessel. As a method which enables treatment even in this case, a method of cutting and removing a stenosed substance such as the thrombus, the plaque, and the calcified lesion is known.

For example, U.S. Pat. No. 9,492,192 discloses a device that transports a cut piece (debris) guided into a catheter in a proximal end direction by cutting the stenosed substance inside the blood vessel and rotating a spiral transport member inside the catheter.

For example, in intravascular treatment of lower limb arteriosclerosis, atherectomy treatment for excising and removing a stenosed site is important for improving arterial patency after the treatment. In particular, a thin blood vessel below a knee is apt to be occluded, and may incur a serious risk to lower limb amputation. Accordingly clinical needs increase. When the stenosed site is cut using an atherectomy device, cut pieces are scattered downstream during the cutting, thereby causing a possibility of vascular occlusion. Therefore, there is a demand for a treatment in which aspiration is performed along with the cutting. However, a catheter that can reach the thin blood vessel below the knee needs to have a relatively small diameter. Consequently, it can be difficult to provide the atherectomy device with a sufficient aspiration function.

SUMMARY

A medical device is disclosed that can be inserted into a relatively thin biological lumen to effectively cut and remove an object.

A medical device is disclosed for removing an object inside a biological lumen. The medical device includes: a rotatable drive shaft; a cutting portion fixed to a distal portion of the drive shaft and configured to cut the object; an outer tube configured to accommodate the drive shaft; a handle unit, the handle unit configured to accommodate a proximal portion of the drive shaft and a proximal portion of the outer tube, the handle unit including an aspiration port configured to discharge a liquid outside of the handle unit, and the aspiration port configured to communicate with an aspiration lumen located between the outer tube and the drive shaft; the drive shaft including a first wire rod helically wound around an axis of the drive shaft, and wherein the first wire rod is configured to directly face an inner peripheral surface of the outer tube; and wherein a helical winding direction of the first wire rod wound toward a proximal end direction of the drive shaft is a reverse direction of a rotation direction of the drive shaft.

In the medical device configured as described above, in a range where the inner peripheral surface of the outer tube and the first wire rod of the drive shaft directly face each other, a helical shape of the first wire rod of the rotating drive shaft enables a force acting toward a proximal side to be applied to a liquid inside the aspiration lumen. Therefore, in the medical device, an aspiration force applied from the handle unit into the aspiration lumen is increased, and the medical device can be inserted into the thin biological lumen to rather effectively cut and remove the object.

In accordance with another aspect, a medical device is disclosed for removing an object inside a biological lumen. The medical device includes: a rotatable drive shaft; a cutting portion fixed to a distal portion of the drive shaft and configured to cut the object inside the biological lumen; an outer tube configured to accommodate the drive shaft; an aspiration lumen located between the outer tube and the drive shaft; and wherein the drive shaft includes a first wire rod helically wound around an axis of the drive shaft, and a helical winding direction of the first wire rod wound toward a proximal end direction of the drive shaft is a reverse direction of a rotation direction of the drive shaft.

In accordance with another aspect, a method is disclosed for cutting and aspirating a lesion area inside a blood vessel. The method includes: inserting a guide wire into the blood vessel and reaching the vicinity of the lesion area with the guide wire; inserting a proximal end of the guide wire onto a guide wire lumen of the medical device, the medical device including a rotatable drive shaft, a cutting portion fixed to a distal portion of the drive shaft, an outer tube accommodating the drive shaft, and a handle unit, the handle unit accommodating a proximal portion of the drive shaft and a proximal portion of the outer tube, the handle unit including an aspiration port, the aspiration port configured to communicate with an aspiration lumen located between the outer tube and the drive shaft, the drive shaft including a first wire rod helically wound around an axis of the drive shaft, and wherein the first wire rod is configured to directly face an inner peripheral surface of the outer tube, and a helical winding direction of the first wire rod wound toward a proximal end direction of the drive shaft is a reverse direction of a rotation direction of the drive shaft; moving the cutting portion of the medical device along the guide wire to the vicinity of the lesion area; delivering a liquid from the handle unit to the vicinity of the lesion area through a distal opening portion of a lumen of the guide wire; and rotating the cutting portion via the drive shaft to cut the lesion area into pieces.

DETAILED DESCRIPTION

Figure 1:
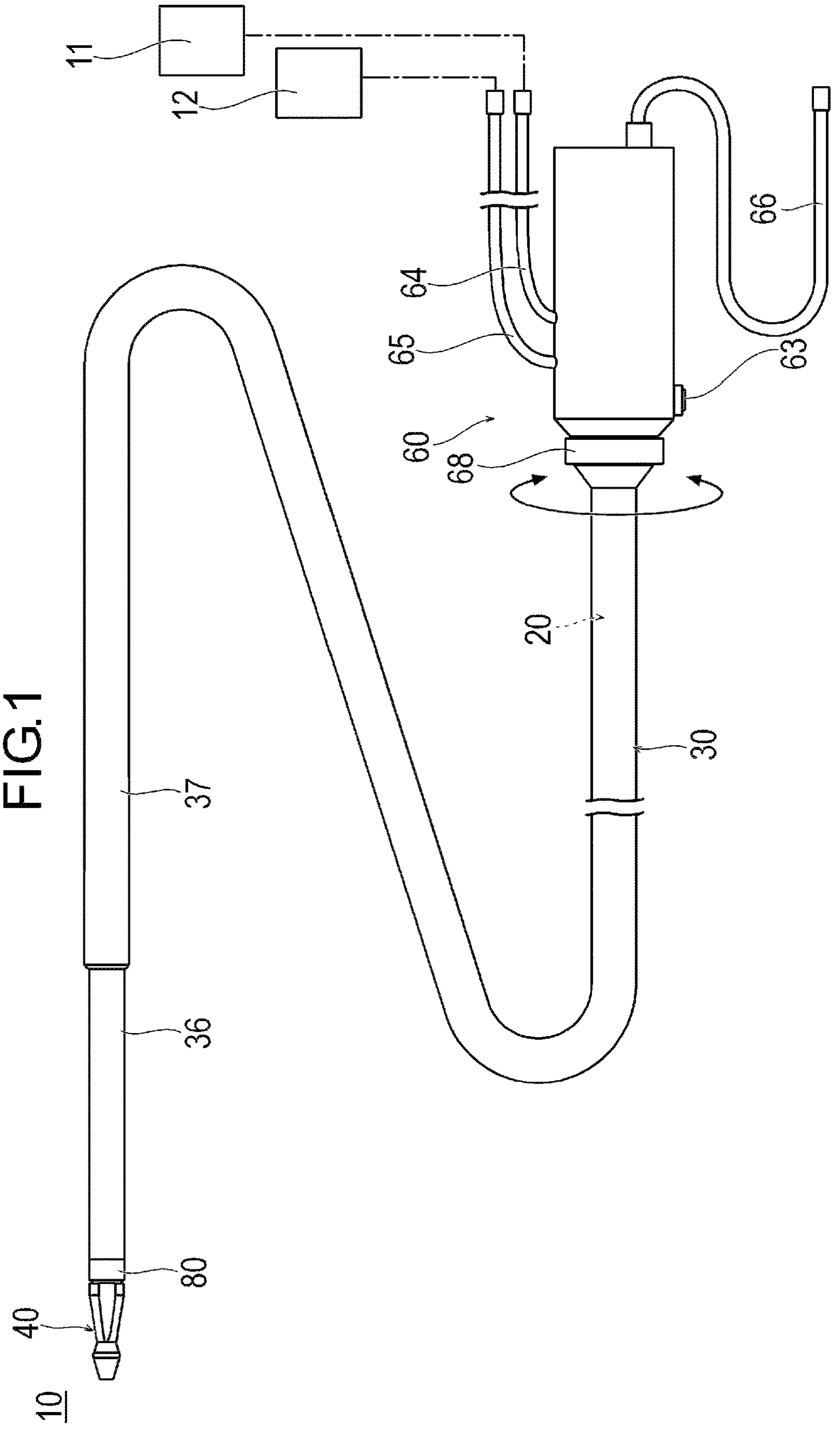
FIG. 1 is a plan view illustrating a medical device according to an exemplary embodiment.

Set forth below with reference to the accompanying drawings is a detailed description of embodiments of a medical device and a method for cutting and aspirating a lesion area inside a blood vessel representing examples of the inventive medical device and method. Note that since embodiments described below are preferred specific examples of the present disclosure, although various technically preferable limitations are given, the scope of the present disclosure is not limited to the embodiments unless otherwise specified in the following descriptions. Dimensions of the drawings may be exaggerated and different from actual dimensions for convenience of description. In addition, in the present specification and the drawings, the same reference numerals will be assigned to configuration elements having substantially the same function, and repeated description will be omitted. In the present specification, a side to be inserted into a lumen will be referred to as a "distal side", and an operator's hand-side will be referred to as a "proximal side".

A medical device 10 according to an exemplary embodiment is inserted into a blood vessel in an acute lower limb ischemia or a deep vein thrombosis, and can be used, for example, for a treatment to cut and remove a plaque or a calcified lesion. An object to be removed is not particularly limited, and may be an atheroma or a thrombus, for example. Furthermore, all objects that may be present inside a biological lumen may correspond to objects to be removed using the medical device 10.

Figure 2:
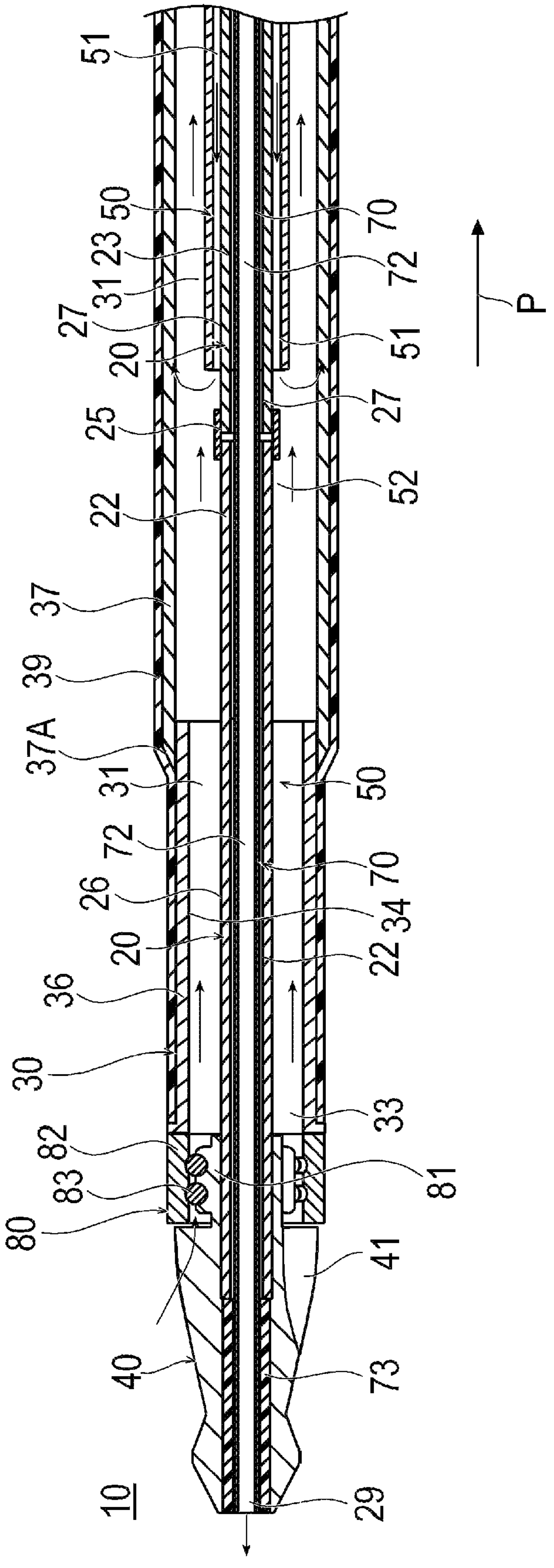
FIG. 2 is a sectional view illustrating a distal portion of the medical device.
Figure 3:
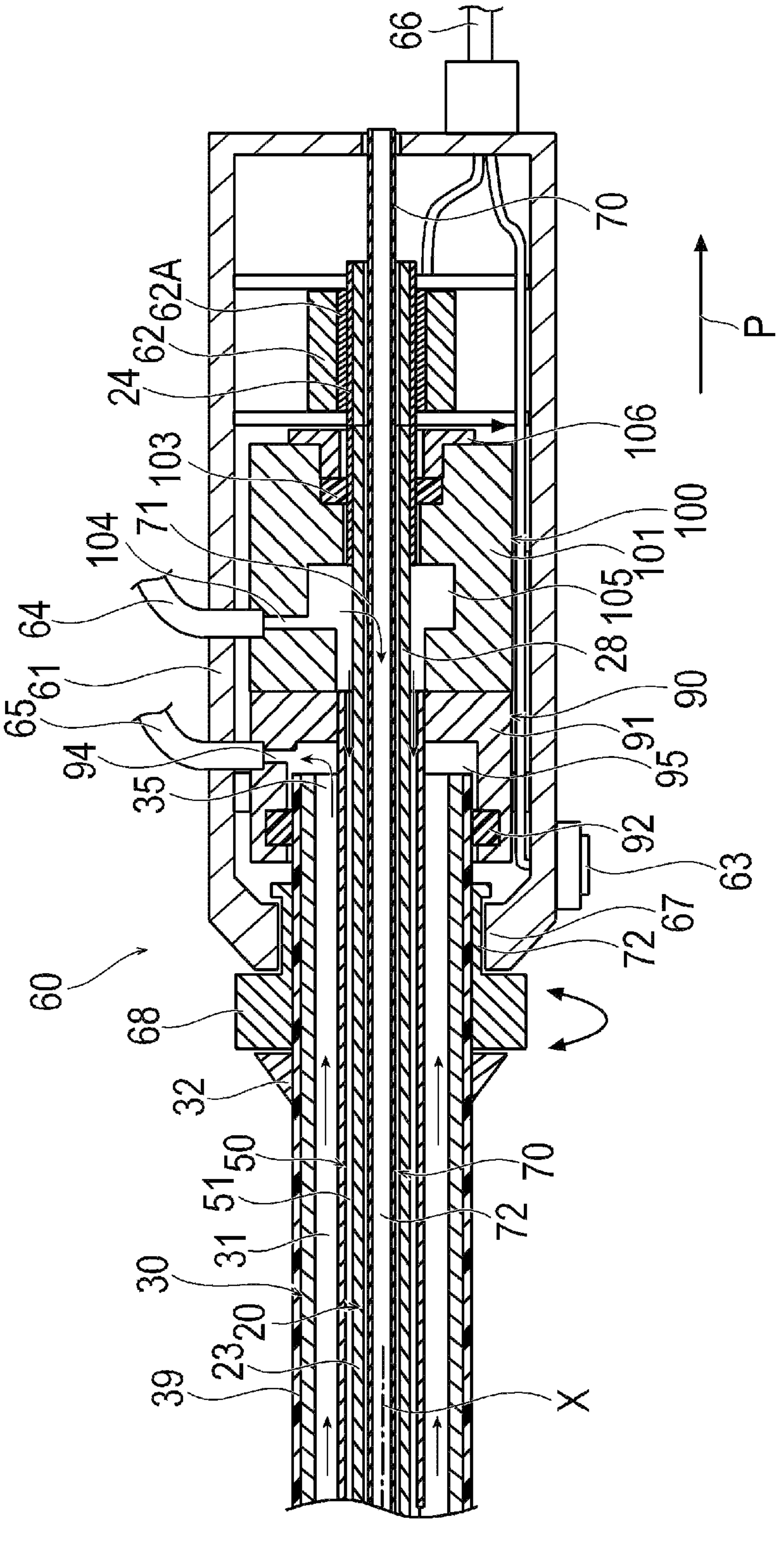
FIG. 3 is a sectional view illustrating a proximal portion of the medical device.
Figure 4A:
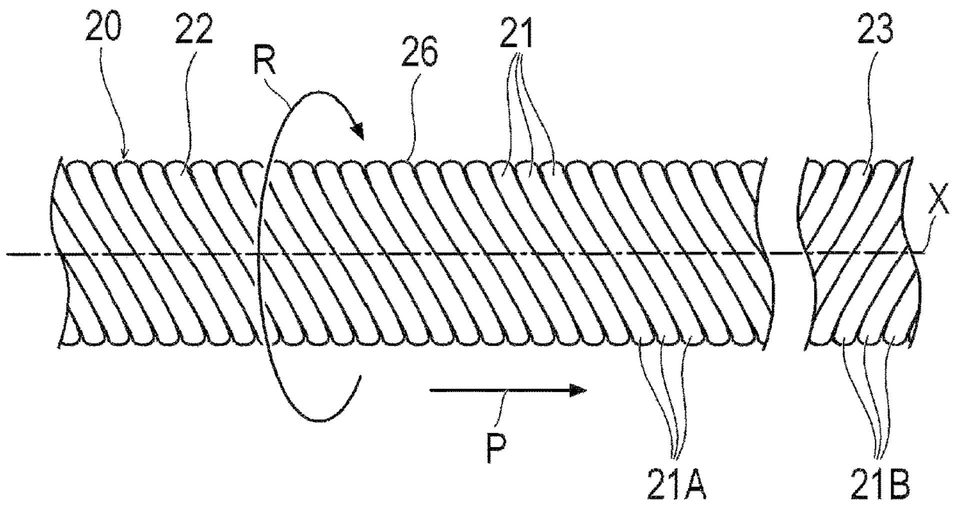
FIG. 4A is a plan view illustrating a drive shaft.
Figure 4B:
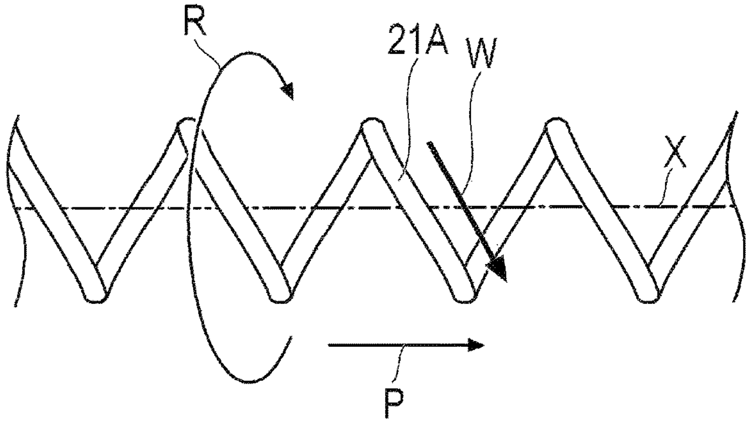
FIG. 4B is a plan view illustrating one wire rod configuring the drive shaft.

As illustrated in FIGS. 1 to 3, the medical device 10 includes a drive shaft 20 that transmits a rotational force, a protective tube 70 accommodated in the drive shaft 20, an inner tube 50 that accommodates the drive shaft 20, and an outer tube 30 that accommodates the drive shaft 20 and the inner tube 50. The medical device 10 further includes a cutting portion 40 that cuts the plaque or the calcified lesion, and a handle unit 60.

As illustrated in FIGS. 2 to 4B, the drive shaft 20 is an elongated tubular body, and transmits the rotational force to the cutting portion 40. The drive shaft 20 includes a first drive shaft 22, a second drive shaft 23 located on a proximal side of the first drive shaft 22, a drive tube 24 fixed to a proximal portion of the second drive shaft 23, and a cylindrical interlock tube 25 that interlocks the first drive shaft 22 and the second drive shaft 23 with each other. A distal end of the drive shaft 20 has a distal opening portion 29 for discharging a liquid.

The first drive shaft 22 and the second drive shaft 23 are flexible, and have a characteristic in which rotational power applied from the proximal side of the first drive shaft 22 and the second drive shaft 23 can be transmitted to the distal side of the first drive shaft 22 and the second drive shaft 23. The cutting portion 40 is fixed to a distal portion of the first drive shaft 22. The first drive shaft 22 and the second drive shaft 23 are tubular bodies in which a plurality of wire rods 21 are aligned and helically interlocked with each other around an axis X of the drive shaft 20. Therefore, the first drive shaft 22 and the second drive shaft 23 allow the liquid to pass through a gap between the wire rods 21. Helical winding directions of the first drive shaft 22 and the second drive shaft 23 are reverse directions to one another. On each outer peripheral surface of the first drive shaft 22 and the second drive shaft 23, an uneven shape that helically (or spirally) extends is formed by the wire rods 21. The wire rod 21 has a first wire rod 21A forming the first drive shaft 22 and a second wire rod 21B forming the second drive shaft 23. The first drive shaft 22 has a first outer peripheral surface 26 that directly faces an inner peripheral surface of the outer tube 30. That is, the inner peripheral surface of the outer tube 30 and the first outer peripheral surface 26 of the first drive shaft 22 directly face each other without interposing another member between the inner peripheral surface of the outer tube 30 and the first outer peripheral surface 26. A helical winding direction W of the first wire rod 21A wound toward a proximal end direction P on the first outer peripheral surface 26 of the drive shaft 20 is a reverse direction of a rotation direction R of the drive shaft 20 (refer to FIG. 4B). The second drive shaft 23 is located on the proximal side of the first drive shaft 22. The second drive shaft 23 has a second outer peripheral surface 27. A helical winding direction of the second wire rod 21B wound toward the proximal end direction P on the second outer peripheral surface 27 of the drive shaft 20 is the same direction as the rotation direction R of the drive shaft 20. The distal portion of the second drive shaft 23 is interlocked with the proximal portion of the first drive shaft 22 inside the outer tube 30 by the interlock tube 25. The proximal portion of the second drive shaft 23 is located inside the handle unit 60.

The interlock tube 25 is a cylindrical tubular body fixed to the outer peripheral surface of the proximal portion of the first drive shaft 22 and the distal portion of the second drive shaft 23. A configuration of the interlock tube 25 is not particularly limited as long as the first drive shaft 22 and the second drive shaft 23 can be interlocked with each other.

The drive tube 24 is fixed to the proximal portion of the second drive shaft 23. The drive tube 24 is a rigid tubular body that receives a rotational torque from a drive unit 62. That is, the drive tube 24 has a role of transmitting the rotational torque received from the drive unit 62 to the flexible second drive shaft 23. The drive tube 24 penetrates the drive unit 62, and rotates inside the drive unit 62 via a rotating drive rotor 62A of the drive unit 62.

The material of the first drive shaft 22 and the second drive shaft 23, for example, can be stainless steel, Ta, Ti, Pt, Au, W, polyolefin such as polyethylene and polypropylene, polyamide, polyester such as polyethylene terephthalate, fluorine-based polymer such as polytetrafluoroethylene (PTFE) and ethylene-tetrafluoroethylene copolymer (ETFE), polyether ether ketone (PEEK), or polyimide. The drive shaft 20 may not be divided into the first drive shaft 22 and the second drive shaft 23 as disclosed, and may be, for example, divided into three or more drive shafts.

The outer diameter of the first drive shaft 22 and the second drive shaft 23 is not limited, and may be 0.3 mm to 1.5 mm, for example. The inner diameter of the first drive shaft 22 and the second drive shaft 23 is not particularly limited, and may be 0.2 mm to 1.4 mm, for example.

As illustrated in FIGS. 2 and 3, the protective tube 70 is a flexible tubular body that covers the inside of the drive shaft 20. The protective tube 70 has a guide wire lumen 72 through which a guide wire passes. The guide wire lumen 72 is a lumen for delivering a liquid such as a saline solution to the distal side of the protective tube 70. The protective tube 70 prevents the guide wire passing through the inside of the drive shaft 20 from directly coming into contact with and rubbing against the first drive shaft 22 and the second drive shaft 23. Inside the handle unit 60, the protective tube 70 has a side hole 71 for allowing the liquid to pass through the handle unit 60 by penetrating the inner peripheral surface of the protective tube 70. The distal portion of the protective tube 70 is fixed to the inner peripheral surface of the cutting portion 40 by using an adhesive layer 73. The distal portion of the protective tube 70 may be fixed to the inner peripheral surface of the distal portion of the drive shaft 20. The protective tube 70 is not fixed to other members (for example, the drive shaft 20 and the handle unit 60) except for the distal portion. Therefore, even if the drive shaft 20 is twisted or a length of the drive shaft 20 is changed, the protective tube 70 can maintain a proper shape inside the drive shaft 20. The protective tube 70 may not be provided.

It is desirable that the material of the protective tube 70 has a certain degree of flexibility and low friction. For example, the material of the protective tube 70 can be a fluorine-based polymer such as polyether ether ketone (PEEK) and PTFE/ETFE, polymethyl methacrylate (PMMA), polyethylene (PE), polyether block acid copolymer (PEBAX), or polyimide, and a combination of fluorine-based polymers and/or a polyimide.

Figure 5:
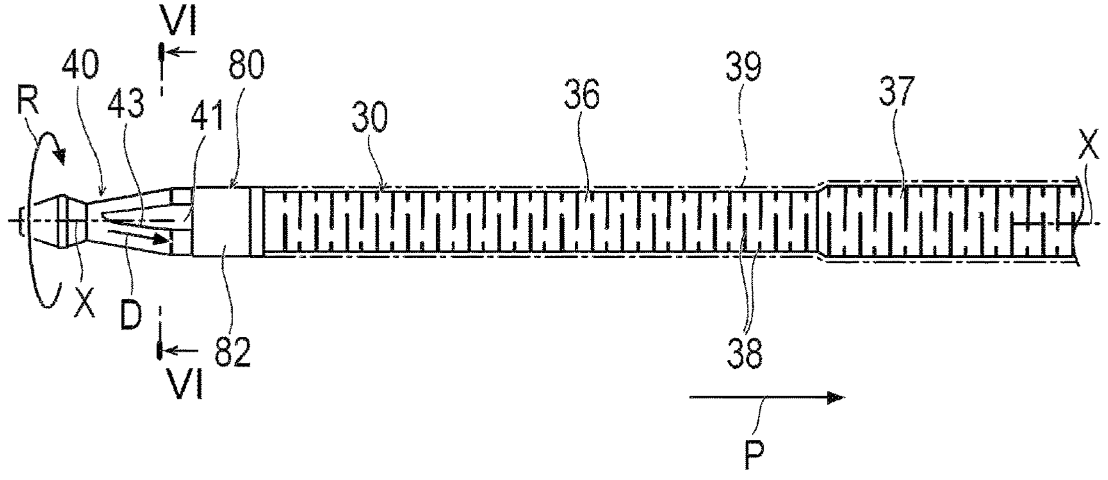
FIG. 5 is a plan view illustrating an outer tube, a bearing, and a cutting portion.
Figure 6:
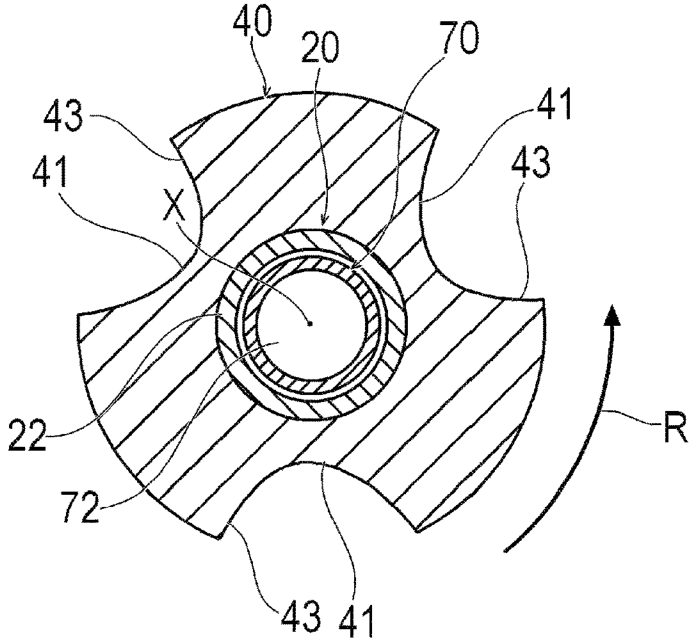
FIG. 6 is a sectional view taken along line VI-VI in FIG. 5.

As illustrated in FIGS. 2, 5, and 6, the cutting portion 40 is a member configured to come into contact with an object such as a plaque and a calcified lesion and to apply a force to reduce a size of the object by cutting the object. Therefore, "cutting" means that the cutting portion 40 comes into contact with a contacting target object and applies the force to reduce the size of the object, and a method of applying the force is not limited. In accordance with an exemplary embodiment, the cutting portion 40 is fixed to the outer peripheral surface of the distal portion of the first drive shaft 22. The surface of the cutting portion 40 can include a plurality of fine abrasive grains. Alternatively, the cutting portion 40 may include a sharp blade.

The material of the cutting portion 40 preferably has strength which enables the plaque, the calcified lesion or the like to be cut. For example, the material of the cutting portion 40 can be stainless steel, Ta, Ti, Pt, Au, W, shape memory alloy, or super steel alloy.

The outer peripheral surface of the cutting portion 40 has a cutout portion 41 that is cut out to have a substantially V-shape in a cross section orthogonal to the axis X. For example, the cutout portions 41 are disposed at an interval of 120 degrees in a circumferential direction. Therefore, for example, the cutting portion 40 can have three cutout portions 41 that are equally aligned in the circumferential direction. An edge portion of each of the cutout portions 41 has a curvature, and can be smoothly formed. The number of the cutout portions 41 is not limited to three.

Each of the cutout portions 41 has a cutout surface 43 directed in the rotation direction R of the cutting portion 40. The cutout surface 43 may be inclined with respect to the axis X of the cutting portion 40. An inclination direction D in which the cutout surface 43 is inclined in the proximal end direction P is a reverse direction of the rotation direction R of the cutting portion 40. In accordance with an embodiment, the cutout surface 43 may not be inclined with respect to the axis X of the cutting portion 40.

As illustrated in FIGS. 2, 3, and 5, the outer tube 30 is a cylindrical body that accommodates the drive shaft 20 and the inner tube 50. An aspiration lumen 31 for aspirating the object whose size is reduced by cutting the plaque, the calcified lesion or the like is formed between the outer tube 30 and the drive shaft 20, and between the outer tube 30 and the inner tube 50.

The distal end of the outer tube 30 has an aspiration opening portion 33 for aspirating the cut object or the liquid discharged from the drive shaft 20. The distal end of the outer tube 30 is located near the proximal end of the cutting portion 40. The proximal end of the outer tube 30 has a proximal opening portion 35 which is open inside the handle unit 60.

The outer tube 30 includes a first outer tube 36 located on the distal side and a second outer tube 37 located on the proximal side of the first outer tube 36. In accordance with an exemplary embodiment, the first outer tube 36 has a substantially constant inner diameter and a substantially constant outer diameter along the axis X. The proximal end of the first outer tube 36 is located on the distal side from the proximal end of the first drive shaft 22. The proximal end of the first outer tube 36 may be located on the proximal side from the proximal end of the first drive shaft 22, or may be located at a position where the first outer tube 36 coincides with the first drive shaft 22. The first outer tube 36 has a first inner peripheral surface 34 that directly faces the first outer peripheral surface 26 of the first drive shaft 22. That is, the first inner peripheral surface 34 and the first outer peripheral surface 26 directly face each other without interposing another member between the first inner peripheral surface 34 of the outer tube 36 and the first outer peripheral surface 26 of the first drive shaft 22. It is preferable that at least 75% of the first inner peripheral surface 34 of the first outer tube 36 directly faces the first outer peripheral surface 26 of the first drive shaft 22. However, the present disclosure is not limited thereto. The distal end of the first outer tube 36 may be fixed to a bearing 80.

The second outer tube 37 has a substantially constant inner diameter and a substantially constant outer diameter along the axis X. The second outer tube 37 has the inner diameter larger than the inner diameter of the first outer tube 36 and the outer diameter of the second outer tube is larger than the outer diameter of the first outer tube 36. The distal portion of the second outer tube 37 is fixed by means of welding, adhesion or the like in a state of being covered with the outer peripheral surface of the proximal portion of the first outer tube 36. Therefore, the inner diameter of the second outer tube 37 substantially coincides with the outer diameter of the first outer tube 36. In accordance with an exemplary embodiment, the distal end of the second outer tube 37 has a tapered portion 37A whose outer diameter decreases in a distal end direction. The proximal end of the second outer tube 37 is located inside the handle unit 60.

An anti-kink protector 32 and an operation unit 68 can be fixed to the outer peripheral surface of the proximal portion of the second outer tube 37. The anti-kink protector 32 helps prevent kinks on the proximal side of the outer tube 30. In the outer tube 30, an aspiration seal portion 92 (to be described later) is in contact with an outer surface on the proximal side from a portion interlocked with the operation unit 68.

A plurality of slits 38 extending in the circumferential direction are formed in the distal side portions of the first outer tube 36 and the second outer tube 37 to be flexibly bent inside the biological lumen. The slit 38 penetrates from the outer peripheral surface to the inner peripheral surface of the tubular body of the outer tube 30. Each of the slits 38 is formed by means of laser processing, for example. Each of the slits 38 is perpendicular to the axis X of the first outer tube 36 and the second outer tube 37, but may not be perpendicular. The slit 38 is formed to have a length smaller than 360 degrees in the circumferential direction of the first outer tube 36 and the second outer tube 37. Therefore, the first outer tube 36 and the second outer tube 37 have a portion that is not cut by the slit 38 per one circumference in order to maintain a shape of the first outer tube 36 and the second outer tube 37. A form of the slit 38 is not limited, and the slit 38 may be spirally formed, for example. In addition, the slit 38 may not be formed. The outer peripheral surface of the first outer tube 36 and the second outer tube 37 includes a coating layer 39. The coating layer 39 prevents the liquid from flowing through the slit 38. For example, the coating layer 39 is formed by a heat shrink tube that shrinks when heated.

The materials of the first outer tube 36 and the second outer tube 37 excluding the coating layer 39 preferably has a certain degree of strength, and for example, the materials of the first outer tube 36 and the second outer tube 37 can be stainless steel, Ta, Ti, Pt, Au, W, shape memory alloy, ABS resin, engineering plastics such as polycarbonate (PC), polymethyl methacrylate (PMMA), polyacetal (POM), polyphenylsulfone (PPSU), polyethylene (PE), carbon fiber, and polyetheretherketone (PEEK), and a combination of the materials.

The outer diameter of the first outer tube 36 is not particularly limited, and may be, for example, 1.00 mm to 1.85 mm. The inner diameter of the first outer tube 36 is not limited, and may be 0.5 mm to 1.75 mm, for example. The length of the first outer tube 36 along the axis X is not particularly limited, and may be, for example, 50 mm to 500 mm.

The outer diameter of the second outer tube 37 is not particularly limited, and may be, for example, 1.65 mm to 2.50 mm. The inner diameter of the second outer tube 37 is not particularly limited, and may be, for example 1.1 mm to 1.95 mm. The length of the second outer tube 37 along the axis X is not particularly limited, and may be, for example, 750 mm to 2,000 mm.

Figure 7:
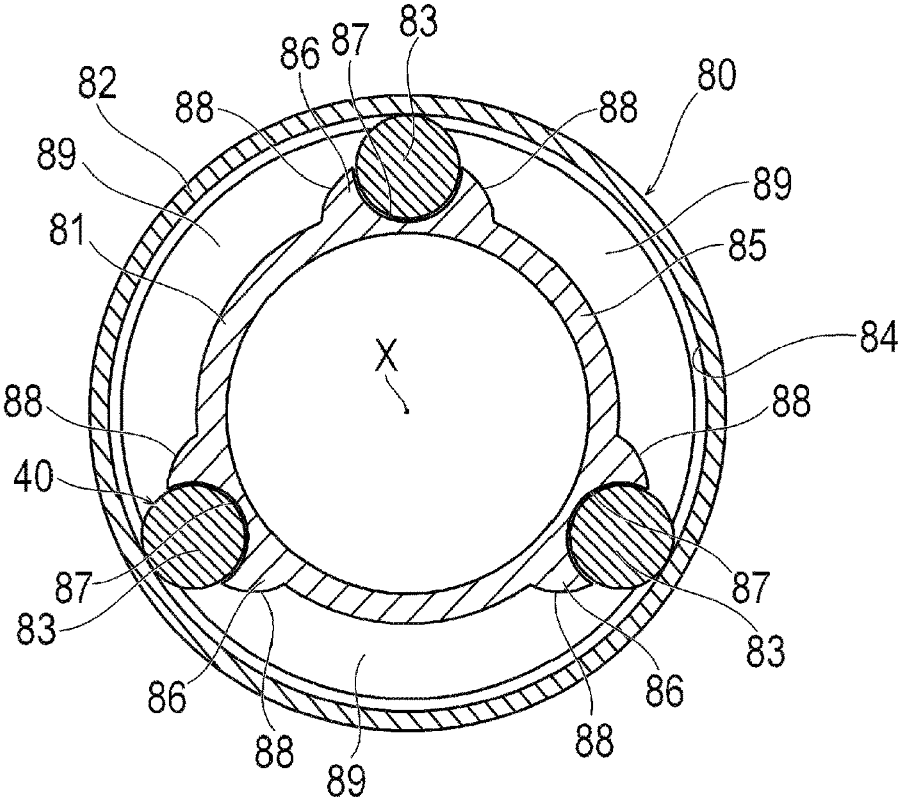
FIG. 7 is a sectional view illustrating the bearing.

As illustrated in FIGS. 2 and 7, the bearing 80 can secure a space between an inner ring 81 and an outer ring 82 in order to circulate the fluid, for example, a liquid and/or gas, or the object such as the reduced plaque or calcified lesion. The bearing 80 includes the cylindrical inner ring 81, the cylindrical outer ring 82 disposed to surround the inner ring 81, and a plurality of rolling elements 83 disposed between the inner ring 81 and the outer ring 82. The inner ring 81 is supported to be rotatable by the outer ring 82 via the rolling elements 83. The inner ring 81 and the outer ring 82 are relatively rotatable around the axis X. The axis X of the drive shaft 20 is also the axis X of the inner ring 81 and the outer ring 82. The outer ring 82 is fixed to the distal end of the first outer tube 36. The inner ring 81 is fixed to the proximal end of the cutting portion 40. The inner ring 81 may be a portion of the cutting portion 40. In addition, the outer ring 82 may be a portion of the outer tube 30.

In accordance with an exemplary embodiment, the rolling element 83 is a spherical body rotatable between the inner ring 81 and the outer ring 82. The rolling element 83 may not be the spherical body as long as the rolling element 83 is rotatable, and may be a columnar member, for example.

The inner peripheral surface of the outer ring 82 includes a groove portion 84 extending in the circumferential direction. The groove portion 84 is a portion with which the rolling element 83 comes into contact and rolling on the groove portion 84. The rolling element 83 moves in the circumferential direction relative to the outer ring 82 by rolling on the groove portion 84. The rolling element 83 can slide on the groove portion 84 instead of rolling on the groove portion 84.

The inner ring 81 includes a cylindrical inner ring main body 85 having a constant outer diameter, and a plurality of accommodation portions 86 disposed on the outer peripheral surface of the inner ring main body 85 and protruding outward in the radial direction. Each of the accommodation portions 86 has a recess portion 87 that accommodates the rotatable rolling element 83. The recess portion 87 is open toward the groove portion 84. The number of the accommodation portions 86 is not particularly limited, and may be, for example, three, which correspond to the number of the cutout portions 41. The number of the accommodation portions 86 may not correspond to the number of the cutout portions 41. As long as the number of the accommodation portions 86 is three or more, positions of the inner ring 81 and the outer ring 82 which are relatively rotated can be satisfactorily maintained. In accordance with an exemplary embodiment, the three accommodation portions 86 are equally disposed in the circumferential direction of the inner ring main body 85. The rolling element 83 smoothly slides inside the recess portion 87. Each of the accommodation portions 86 has two side wall surfaces 88 directed in the circumferential direction. A passage 89 that penetrates along the axis X is formed between the accommodation portions 86 which are adjacent to each other in the circumferential direction. The passage 89 is defined by the side wall surface 88 of the accommodation portion 86 adjacent in the circumferential direction, the outer peripheral surface of the inner ring 81, and the inner peripheral surface of the outer ring 82. The passage 89 and the aspiration lumen 31 overlap each other in a direction parallel to the axis X. Therefore, both of the passage 89 and the aspiration lumen 31 have a coincident range when viewed from the distal side.

As illustrated in FIGS. 2 and 3, the inner tube 50 is a flexible tubular body that surrounds the second drive shaft 23 inside the outer tube 30. The distal end of the inner tube 50 is located on the proximal side from the distal end of the second drive shaft 23. In accordance with an exemplary embodiment, the proximal end of the inner tube 50 is fixed to the handle unit 60. A liquid delivering lumen 51 that delivers the liquid in the distal end direction is formed between the inner tube 50 and the second drive shaft 23. The drive shaft 20 located inside the inner tube 50 enables the liquid to pass through a gap of the wire rods 21 between the inner peripheral surface and the outer peripheral surface of the wire rods 21. Therefore, a gap between the drive shaft 20 and the protective tube 70 also functions as the liquid delivering lumen 51. Inside the outer tube 30, the liquid delivering lumen 51 is located inside the inner tube 50, and the aspiration lumen 31 is located outside the inner tube 50. The inner tube 50 helps prevents the fluid from leaking out to the aspiration lumen 31 from the liquid delivering lumen 51, and can rather effectively transmit the aspiration pressure and the liquid delivering pressure of the handle unit 60 to the distal side of the inner tube 50.

It is desirable that the material of the inner tube 50 has a certain degree of flexibility and low friction. The material of the inner tube 50 can be a fluorine-based polymer such as polyether ether ketone (PEEK) and PTFE/ETFE, polymethyl methacrylate (PMMA), polyethylene (PE), polyether block acid copolymer (PEBAX), or polyimide, and a combination of the materials.

As illustrated in FIGS. 1 and 3, the handle unit 60 includes a casing 61, a drive unit 62, a switch 63, a liquid delivering port 64, an aspiration port 65, and an electric cable 66. The handle unit 60 further includes an operation unit 68, an aspiration portion 90, and a liquid delivering portion 100.

The casing 61 accommodates the drive unit 62, the liquid delivering portion 100, and the aspiration portion 90. A bearing-shaped first support portion 67 supports the rotatable operation unit 68 in the distal portion of the casing 61.

For example, the drive unit 62 can be a hollow motor. The drive unit 62 is rotated by electric power supplied from the outside via the electric cable 66. The drive tube 24 of the drive shaft 20 penetrates through the drive unit 62. The drive tube 24 is directly connected to a hollow drive rotor 62A of the hollow motor. A rotation speed of the drive unit 62 is not particularly limited. For example, the rotation speed may be, for example, 5,000 rpm (revolutions per minute) to 200,000 rpm. The configuration of the drive unit 62 is not particularly limited.

The electric cable 66 can be connected to an external power source or a control apparatus. The switch 63 is a portion by which an operator operates driving and stopping the drive unit 62.

The operation unit 68 is operated by the operator, for example, with a finger to apply a rotational torque to the outer tube 30. The operation unit 68 is fixed to the outer peripheral surface of the proximal portion of the outer tube 30.

The liquid delivering port 64 can be connected to a liquid delivering source 11 such as an external liquid delivering pump. A liquid such as a saline solution to be delivered into the living body is supplied from the liquid delivering source 11 to the liquid delivering port 64. The liquid delivering port 64 transports the supplied liquid to the liquid delivering portion 100. The liquid delivering source 11 may have any configuration as long as the liquid delivering pressure can be generated, for example, the liquid delivering pressure can be delivered using a pump, a bag suspended in a drip tower, or a syringe. In accordance with an exemplary embodiment, the liquid delivering source 11 configured to actively delivering the liquid, for example, a pump, can be used. Accordingly, with the use of a pump, for example, the liquid delivering amount can be stabilized.

The aspiration port 65 can be connected to an aspiration source 12, for example, an external aspiration pump. The aspiration port 65 transports the liquid or the like aspirated by the aspiration source 12 and contained inside the aspiration portion 90, toward the aspiration source 12. The aspiration source 12 may have any configuration as long as the aspiration pressure can be generated, and a pump or a syringe may be used, for example. The aspiration source 12 capable of actively aspirating the fluid, such as the pump, for example, may be used. Accordingly, the aspiration pressure can be increased, and the aspiration force can be stabilized and improved.

The aspiration portion 90 applies the aspiration pressure to the aspiration lumen 31 of the outer tube 30. The aspiration portion 90 includes a first housing 91 and an aspiration seal portion 92.

The first housing 91 includes an aspiration port 94 that discharges the liquid to the outside, and a first space portion 95 that communicates with the aspiration port 94. The proximal opening portion 35 of the outer tube 30 is located inside the first space portion 95. The inner tube 50 is fixed to the proximal portion of the first space portion 95. The aspiration port 94 is connected to the aspiration port 65.

The aspiration seal portion 92 is located between the first housing 91 and the outer tube 30 in the distal portion of the first space portion 95. The aspiration seal portion 92 helps prevent external air from flowing into the first space portion 95. Furthermore, the aspiration seal portion 92 supports the outer tube 30 to be rotatable.

The liquid delivering portion 100 is located on the proximal side of the aspiration portion 90, and is located on the distal side of the drive unit 62. The liquid delivering portion 100 delivers the liquid to the liquid delivering lumen 51 and the guide wire lumen 72. The liquid delivering portion 100 includes a second housing 101, a liquid delivering seal portion 103, and a fixing member 106.

The second housing 101 includes a liquid delivering port 104 through which the liquid is delivered from the outside, and a second space portion 105 that communicates with the liquid delivering port 104. The drive shaft 20 penetrates through the inside of the second space portion 105. A side hole 71 through which the liquid is delivered to the guide wire lumen 72 is located inside the second space portion 105. The liquid delivering port 104 is connected to the liquid delivering port 64.

The liquid delivering seal portion 103 is located between the second housing 101 and the drive tube 24 of the drive shaft 20 in the proximal portion of the second space portion 105. The liquid delivering seal portion 103 helps prevent the liquid pressurized inside the second space portion 105 from flowing outward. In accordance with an exemplary embodiment, the fixing member 106 may be a cylindrical member that fixes the liquid delivering seal portion 103 to the second housing 101.

Next, a method of using the medical device 10 according to the present embodiment will be described as an example with reference to a case of cutting and aspirating a lesion area such as the plaque and the calcified lesion inside the blood vessel.

Figure 8:
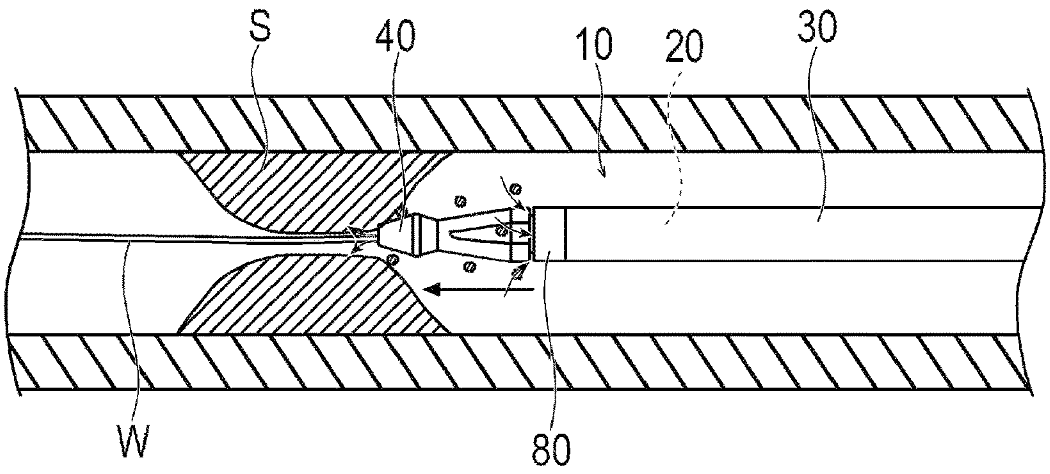
FIG. 8 is a schematic view illustrating a state where cutting is performed using the medical device.

First, an operator inserts a guide wire W into the blood vessel so that the guide wire W reaches the vicinity of a lesion area S. Next, the operator inserts the proximal end of the guide wire W into the guide wire lumen 72 of the medical device 10. Thereafter, as illustrated in FIG. 8, the cutting portion 40 is moved to the vicinity of the lesion area S through a guide of the guide wire W.

Next, as illustrated in FIGS. 1 to 3, the operator operates the switch 63 to start liquid delivering and aspirating. That is, the operator operates the external liquid delivering source 11 and the aspiration source 12. Simultaneously or after a lapse of a prescribed time, the cutting portion 40 is rotated via the drive shaft 20. In this manner, the operator can cut the lesion area S by using the cutting portion 40.

The operator can operate the operation unit 68 in a case where the operator wants to change a position of the cutting portion 40 in the circumferential direction. When the operator rotates the operation unit 68, the operation unit 68 supported by the first support portion 67 is rotated. In this manner, the operator can change the position of the cutting portion 40 inside the blood vessel. Furthermore, the operator moves the whole handle unit 60 or the extracorporeally exposed outer tube 30, and causes the outer tube 30 to reciprocate along a longitudinal direction of the blood vessel. In this manner, the operator can cut the lesion area S along the longitudinal direction of the blood vessel by using the cutting portion 40. The first outer tube 36 is relatively thin. Accordingly, the first outer tube 36 can be inserted into a relatively thin biological lumen. Therefore, the cutting portion 40 can cut the lesion area S having the relatively thin biological lumen into relatively small cut pieces (debris).

When the liquid delivering starts, the saline solution flowing into the second space portion 105 from the liquid delivering port 104 enters the liquid delivering lumen 51 inside the inner tube 50. Furthermore, the saline solution flowing into the second space portion 105 flows into the drive shaft 20 through the gap between the wire rods 21 of the drive shaft 20. The saline solution flowing into the drive shaft 20 flows into a lumen (portion of the liquid delivering lumen 51) between the drive shaft 20 and the protective tube 70, and flows into the guide wire lumen 72 inside the protective tube 70 from the side hole 71. The drive shaft 20 and the second housing 101 are sealed by the liquid delivering seal portion 103. Therefore, the saline solution in the second space portion 105 is unlikely to flow out from between the drive shaft 20 and the second housing 101. Therefore, the second space portion 105 can maintain the relatively high liquid delivering pressure.

The saline solution entering the liquid delivering lumen 51 and the guide wire lumen 72 moves to the distal side. When the saline solution inside the liquid delivering lumen 51 reaches the distal side of the inner tube 50, the saline solution moves to the aspiration lumen 31.

The saline solution inside the guide wire lumen 72 is discharged into the blood vessel through the distal opening portion 29. A portion of the saline solution entering the inside of the blood vessel is aspirated into the aspiration lumen 31 of the outer tube 30 together with the blood and the cut object. The object and the liquid which enter the aspiration lumen 31 move to the proximal side through the aspiration lumen 31. As illustrated in FIG. 2, the liquid entering the aspiration lumen 31 is diluted by the saline solution merging from the liquid delivering lumen 51 on the distal side of the inner tube 50. Therefore, the thrombus can be prevented from being formed inside the aspiration lumen 31, and an aspiration amount can be increased by lowering viscosity of the aspirated object. Therefore, aspiration performance can be improved while a decreases in the aspiration force of the medical device 10 or damage to the medical device 10 can be prevented. In addition, the thrombus formed inside the medical device 10 can be prevented from flowing out into the biological lumen. When the liquid entering the aspiration lumen 31 reaches the first space portion 95 of the aspiration portion 90, the fluid is discharged from the aspiration port 94 to the external aspiration source 12. The first housing 91 of the aspiration portion 90 and the outer tube 30 are sealed by the aspiration seal portion 92. Therefore, it is possible to prevent a decrease in the aspiration pressure of the first space portion 95. The aspiration pressure at this time may be, for example, 0 kPa to 90 kPa, and preferably 0 kPa to 50 kPa, when absolute vacuum is set to 0 kPa.

After the lesion area S is completely cut and aspirated, the operator presses the switch 63. In this manner, the rotation of the drive shaft 20 is stopped, and the cutting by the cutting portion 40 is stopped. Simultaneously or after a lapse of a prescribed time, the liquid delivering and the aspirating are stopped. That is, the external liquid delivering source 11 and the aspiration source 12 are stopped. Thereafter, the medical device 10 is removed from the blood vessel, and the treatment is completed.

As described above, according to the present embodiment, a medical device 10 is disclosed for removing the object inside the biological lumen. The medical device 10 includes the rotatable drive shaft 20, the cutting portion 40 fixed to the distal portion of the drive shaft 20 to cut the object by coming into contact with the object, the outer tube 30 that accommodates the drive shaft 20 to be rotatable, and the handle unit 60 disposed in the proximal portion of the drive shaft 20 and the outer tube 30. The handle unit 60 has the aspiration port 94 for discharging the liquid to the outside, and the aspiration port 94 communicates with the aspiration lumen 31 between the outer tube 30 and the drive shaft 20. The drive shaft 20 has at least one first wire rod 21A helically wound around the axis X of the drive shaft 20. The drive shaft 20 has the first outer peripheral surface 26 that directly faces the inner peripheral surface of the outer tube 30. The helical winding direction W in which the first wire rod 21A is wound in the proximal end direction P is the reverse direction of the rotation direction R of the drive shaft 20. The first wire rod 21A directly faces the inner peripheral surface of the outer tube 30.

In the medical device 10 configured as described above, in a range where the inner peripheral surface of the outer tube 30 and the first wire rod 21A of the drive shaft 20 directly face each other, a helical shape of the first wire rod 21A of the rotating drive shaft 20 enables a force acting toward the proximal side to be applied to the liquid inside the aspiration lumen 31. That is, the helical winding direction W of the first wire rod 21A is the reverse direction of the rotation direction R of the drive shaft 20. Accordingly, when the drive shaft 20 is rotated, the helical first wire rod 21A can push the fluid or the object in contact with the first wire rod 21A in the proximal end direction P (refer to FIG. 4B). Therefore, in the medical device 10, the aspiration force applied from the handle unit 60 into the aspiration lumen 31 can be increased, and the object can be rather effectively cut and removed inside the relatively thin biological lumen.

In addition, the first wire rod 21A directly faces the inner peripheral surface of the distal portion of the outer tube 30. Therefore, the medical device 10 can effectively increase the aspiration force inside the distal portion of the outer tube 30.

In addition, the outer tube 30 has the first outer tube 36 and the second outer tube 37 located on the proximal side of the first outer tube 36. The inner diameter of the first outer tube 36 is smaller than the inner diameter of the second outer tube 37, and the outer diameter of the first outer tube 36 is smaller than the outer diameter of the second outer tube 37. In this manner, the medical device 10 has improved passing ability of the first outer tube 36 located on the distal side and having the small outer diameter, and can be operated by being inserted into the thin biological lumen. In addition, the medical device 10 can improve pushing performance, and can increase the aspiration force by using the second outer tube 37 located on the proximal side of the first outer tube 36 and having the large outer diameter and inner diameter.

In addition, the first wire rod 21A directly faces the inner peripheral surface of the first outer tube 36 and the inner peripheral surface of the second outer tube 37. In this manner, the first wire rod 21A that increases the aspiration force is disposed on both the inside of the first outer tube 36 on which the aspiration force is less likely to be applied from the proximal side due the small inner diameter and the inside of the second outer tube 37 on which the aspiration force is likely to be applied from the proximal side due to the large inner diameter. The gap is small between the inner peripheral surface of the first outer tube 36 and the first outer peripheral surface 26 where the first wire rod 21A is located. Accordingly, the influence of the spiral uneven shape of the first outer peripheral surface 26 on the liquid in the gap is relatively great compared to a case where the gap is relatively large. Therefore, the first wire rod 21A faces a portion of the second outer tube 37 on the further proximal side from the proximal end of the first outer tube 36 to which the aspiration force is less likely to be applied from the proximal side due to the small inner diameter, and can effectively increase the aspiration force. It is preferable, for example, that at least 75% of the inner peripheral surface of the first outer tube 36 directly faces the first wire rod 21A.

In addition, the medical device 10 has the protective tube 70 located inside the drive shaft 20. The handle unit 60 has the liquid delivering port 104 through which the liquid is delivered from the outside. The liquid delivering port 104 communicates with the guide wire lumen 72 inside the protective tube 70. In this manner, the medical device 10 can deliver the liquid via the guide wire lumen 72 of the protective tube 70 located inside the drive shaft 20. The protective tube 70 is located inside the drive shaft 20 where pressure loss is likely to occur due to liquid flowing from the gap of the wire rods 21. Accordingly, the pressure loss caused by the liquid flowing in the drive shaft 20 can be prevented, and the liquid can be delivered with less pressure loss. In this case, the protective tube 70 helps prevent the liquid flowing in the distal end direction of the guide wire lumen 72 from passing to the outer peripheral surface from the inner peripheral surface of the drive shaft 20.

In addition, the passage 89 located between the accommodation portions 86 adjacent to each other in the rotation direction R of the drive shaft 20 communicates with the aspiration lumen 31. In this manner, the aspiration force supplied from the aspiration lumen 31 can be effectively applied to the distal side via the passage 89 that communicates with the aspiration lumen 31. The space inside the passage 89 may overlap the space inside the aspiration lumen 31 in the direction parallel to the axis X of the drive shaft 20. That is, when viewed from the distal side (or the proximal side), at least a portion of the space inside the passage 89 may overlap the space inside the aspiration lumen 31. In this manner, the aspiration force supplied from the aspiration lumen 31 can be rather effectively applied to the distal side via the passage 89.

In addition, the cutting portion 40 has the cutout portion 41 formed to be recessed on the outer peripheral surface of the cutting portion 40 and communicating with the aspiration lumen 31. The cutout portion 41 has the cutout surface 43 directed in the rotation direction R of the cutting portion 40. The cutout surface 43 is inclined with respect to the line parallel to the axis X of the cutting portion 40. The inclination direction D in which the cutout surface 43 is inclined in the proximal end direction P is the reverse direction of the rotation direction R of the cutting portion 40. In this manner, when the cutting portion 40 is rotated, the cutout surface 43 inclined with respect to the line parallel to the axis X can push the fluid or the object in contact with the cutout surface 43 in the proximal end direction P. Therefore, the cutting portion 40 can deliver the fluid located in the recessed cutout portion 41 to the proximal side by using the cutout surface 43. Therefore, the aspiration force applied from the handle unit 60 into the aspiration lumen 31 is increased, and the cut object can be effectively aspirated.

In addition, the drive shaft 20 has the first drive shaft 22 including the first wire rod 21A that directly faces the inner peripheral surface of the outer tube 30, and the second drive shaft 23 including the second wire rod 21B, located on the proximal side of the first drive shaft 22, and interlocked with the first drive shaft 22. The winding direction of the second wire rod 21B is the reverse direction of the winding direction W of the first wire rod 21A. In this manner, for example, when the drive shaft 20 is rotated, and a force is applied to the first drive shaft 22 in an unwinding direction so that the first drive shaft 22 shrinks (or shortens) in the direction of the axis X. In contrast, a force is applied to the second drive shaft 23 in an opposite winding direction so that the second drive shaft 23 stretches (or extends) in the direction of the axis X. Therefore, for example, the shrinking (or shortening) of the first drive shaft 22 can be absorbed by the stretching (or extending) of the second drive shaft 23, and a change in the entire length of the drive shaft 20 can be prevented. Therefore, the position of the drive shaft 20 and the cutting portion 40 can be held at the proper position with respect to other members, and proper operations (for example, rotation, cutting, liquid delivering, or aspiration) of the medical device 10 can be maintained.

In addition, the inner tube 50 is disposed between the second drive shaft 23 and the outer tube 30, and the proximal portion of the inner tube 50 is fixed to the handle unit 60. In this manner, the spiral shape of the outer peripheral surface of the second drive shaft 23 can help prevent a decrease in the aspiration force. Therefore, the inner tube 50 effectively transmits the aspiration pressure and the liquid delivering pressure of the handle unit 60 to the distal side of the inner tube 50.

The present disclosure is not limited to the above-described embodiments, and various modifications can be made by those skilled in the art within the technical idea of the present disclosure. For example, the biological lumen into which the medical device 10 is inserted is not limited to the blood vessel, and may be a vessel, a ureter, a bile duct, a fallopian tube, or a hepatic duct, for example.

In addition, the first housing 91 and the second housing 101 may be integrally formed. In addition, the aspiration port 94 of the aspiration portion 90 may be open to the atmospheric pressure without being connected to the aspiration source 12. Even according to this configuration, in a case where the pressure inside the biological lumen is higher than the atmospheric pressure, the aspiration portion 90 can aspirate the object inside the biological lumen.

Figure 9:
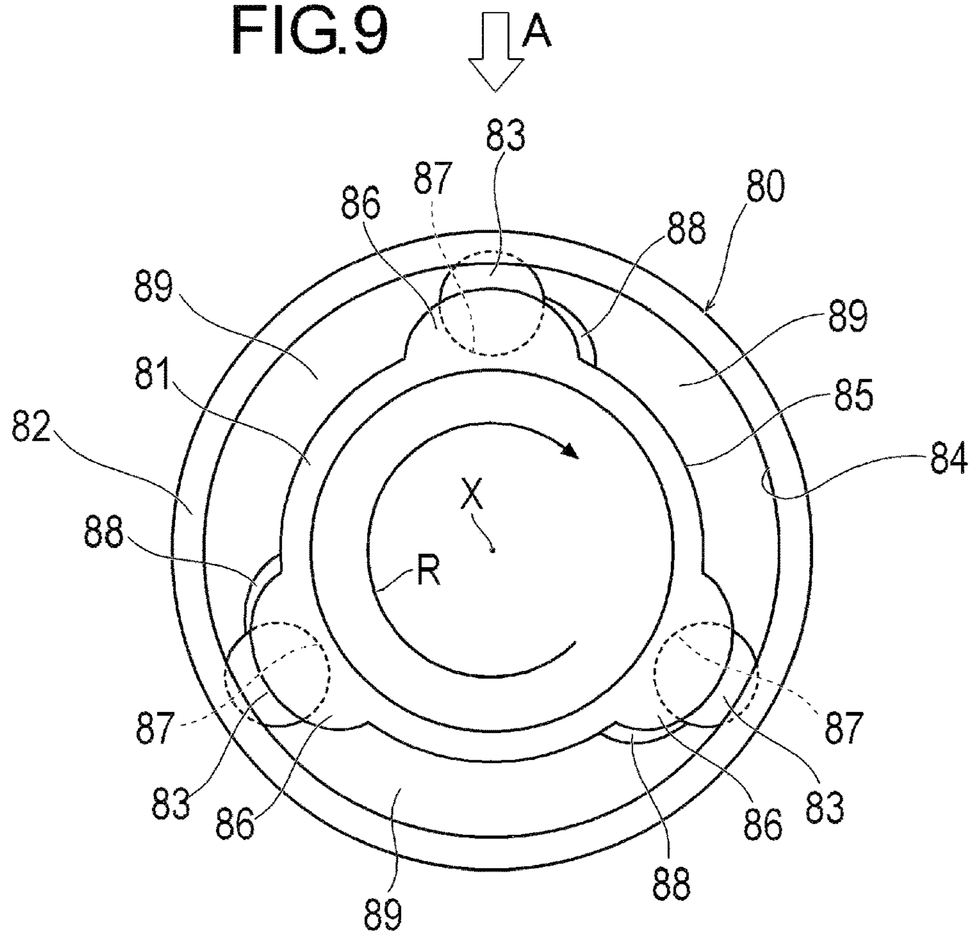
FIG. 9 is a plan view illustrating a modification example of the bearing.
Figure 10:
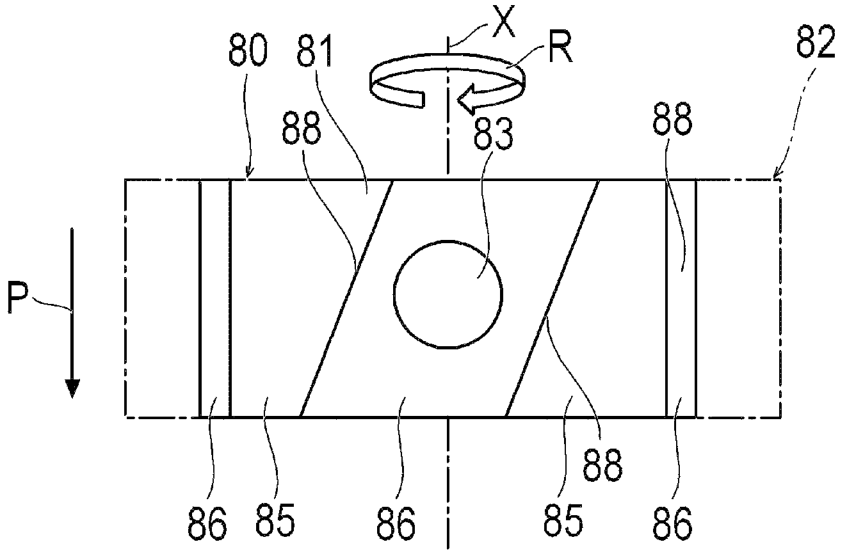
FIG. 10 is a transparent view when an outer ring is transparently viewed from an arrow A in FIG. 9.

In addition, as in the modification example illustrated in FIGS. 9 and 10, the medical device 10 has the bearing 80 disposed in the distal portion of the outer tube 30 and supporting the drive shaft 20 or the cutting portion 40 to be rotatable. The bearing 80 has the plurality of accommodation portions 86 disposed with a gap in the circumferential direction, rotatable together with the drive shaft 20, and having the recess portion 87 which is open outward in the radial direction, and the rolling element 83 accommodated to be rotatable in the recess portion 87. The plurality of accommodation portions 86 have the side wall surface 88 directed in the rotation direction R of the drive shaft 20 and inclined with respect to the axis X of the drive shaft 20. The inclination direction D of the side wall surface 88 with respect to the axis X may be directed in the proximal end direction P, and may be the reverse direction of the rotation direction R of the drive shaft 20. In this manner, the side wall surface 88 of the accommodation portion 86 rotated together with the drive shaft 20 can apply the force acting toward the proximal side to the fluid inside the aspiration lumen 31. Therefore, the aspiration force applied from the handle unit 60 into the aspiration lumen 31 is increased, and the object whose size is cut and reduced by the cutting portion 40 can be effectively aspirated.

Figure 11:
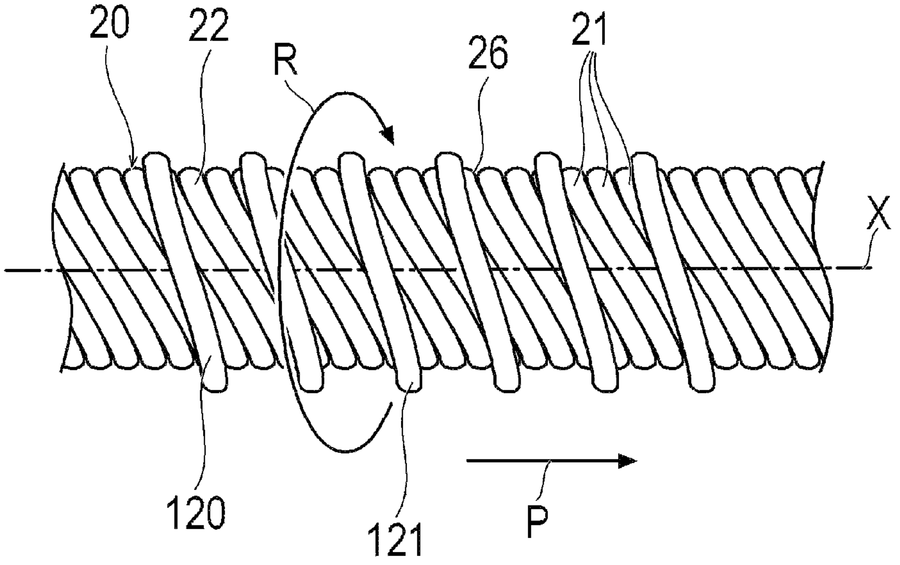
FIG. 11 is a plan view illustrating a modification example of the drive shaft.

In addition, as in another modification example illustrated in FIG. 11, the drive shaft 20 may have an additional coil 120 partially disposed on the outer peripheral surface of the drive shaft 20. The helical winding direction in which a first wire rod 121 forming the additional coil 120 is wound in the proximal end direction P is the reverse direction of the rotation direction R of the drive shaft 20. In this manner, the additional coil 120 can be rotated to push the fluid or the object in contact with the additional coil 120 in the proximal end direction P. Therefore, the medical device 10 can deliver the fluid inside the aspiration lumen 31 to the proximal side by using the additional coil 120 rotated together with the drive shaft 20. Therefore, the aspiration force applied from the handle unit 60 into the aspiration lumen 31 is increased, and the cut object can be effectively aspirated. In a case where the additional coil 120 is provided, the winding direction of a coil located inside the additional coil 120 is not limited. In addition, a shaft disposed inside the additional coil 120 may not be formed by the coil. For example, the shaft disposed inside the additional coil 120 may be a wire braided tube.

In addition, the inner peripheral surfaces of the first outer tube 36 and/or the second outer tube 37 may have a stationary vane for preventing the fluid from flowing in the rotation direction R. For example, the stationary vane may be a projection portion extending along the axis X on the inner peripheral surfaces of the first outer tube 36 and/or the second outer tube 37. The stationary vane can help prevent the fluid from flowing in the rotation direction R, can increase the flow along the axis X, and can increase the aspiration force.

The detailed description above describes embodiments of a medical device and a method for cutting and aspirating a lesion area inside a blood vessel representing examples of the inventive medical device and method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device for removing an object inside a biological lumen, comprising:
- a rotatable drive shaft;
- a cutting portion fixed to a distal portion of the drive shaft and configured to cut the object;
- an outer tube configured to accommodate the drive shaft;
- a handle unit, the handle unit configured to accommodate a proximal portion of the drive shaft and a proximal portion of the outer tube, the handle unit including an aspiration port configured to discharge a liquid outside of the handle unit, and the aspiration port configured to communicate with an aspiration lumen located between the outer tube and the drive shaft;
- the drive shaft including a first wire rod helically wound around an axis of the drive shaft, and wherein the first wire rod is configured to directly face an inner peripheral surface of the outer tube;
- wherein a helical winding direction of the first wire rod wound toward a proximal end direction of the drive shaft is a reverse direction of a rotational direction of the drive shaft;
- the drive shaft includes a first drive shaft including the first wire rod and a second drive shaft including a second wire rod, and a distal end of the second drive shaft is located proximal to a proximal end of the first drive shaft, and the proximal end of the first drive shaft is interlocked with the distal end of the second drive shaft;
- a winding direction of the second wire rod being a reverse direction of the winding direction of the first wire rod;
- an inner tube disposed between the second drive shaft and the outer tube;
- a lumen formed between the inner tube and the second drive shaft, and wherein the lumen formed between the inner tube and the second drive shaft is a liquid delivering lumen that delivers a liquid in a distal direction; and
- wherein a distal end of the inner tube is located on a proximal side of the distal end of the second drive shaft, and a proximal portion of the inner tube is fixed to the handle unit.

2. The medical device according to claim 1,
- wherein the first wire rod is configured to directly face an inner peripheral surface of a distal portion of the outer tube.

3. The medical device according to claim 1,
- wherein the outer tube includes a first outer tube and a second outer tube located on a proximal side of the first outer tube;
- an inner diameter of the first outer tube being smaller than an inner diameter of the second outer tube; and
- an outer diameter of the first outer tube being smaller than an outer diameter of the second outer tube.

4. The medical device according to claim 3,
- wherein the first wire rod is configured to directly face an inner peripheral surface of the first outer tube and an inner peripheral surface of the second outer tube.

5. The medical device according to claim 1, further comprising:
- a bearing disposed in a distal portion of the outer tube, and configured to support the rotatable drive shaft or the cutting portion;
- wherein the bearing is disposed with a gap in a circumferential direction, and is configured to be rotatable together with the rotatable drive shaft, and wherein the bearing includes a plurality of accommodation portions having a recess portion which is open outward in a radial direction, and a rotatable rolling element configured to be accommodated in the recess portion; and
- wherein each accommodation portion has a side wall surface directed in the rotational direction of the drive shaft and inclined with respect to the axis of the drive shaft, and an inclination direction of the side wall surface with respect to the axis is directed in a proximal end direction, and is the reverse direction of the rotational direction of the drive shaft.

6. The medical device according to claim 5, further comprising:
- a passage located between the accommodation portions adjacent to each other in the rotation direction of the drive shaft and configured to communicate with the aspiration lumen.

7. The medical device according to claim 1,
- wherein the cutting portion includes a recessed cutout portion on an outer peripheral surface of the cutting portion, and configured to communicate with the aspiration lumen;
- wherein the cutout portion includes a cutout surface directed in a rotational direction of the cutting portion;
- wherein the cutout surface is inclined with respect to a line parallel to an axis of the cutting portion; and
- wherein an inclination direction in which the cutout surface is inclined in the proximal end direction is the reverse direction of the rotational direction of the cutting portion.

8. The medical device according to claim 1, wherein the drive shaft includes an additional coil partially disposed on an outer peripheral surface of the drive shaft, and a helical winding direction of the additional coil wound toward the proximal end direction of the drive shaft is the reverse direction of the rotational direction of the drive shaft.

9. A method for cutting and aspirating a lesion area inside a blood vessel with the medical device of claim 1, the method comprising:

inserting a guide wire into the blood vessel and reaching the vicinity of the lesion area with the guide wire;

inserting a proximal end of the guide wire into a guide wire lumen of the medical device;

moving a cutting portion of the medical device along the guide wire to the vicinity of the lesion area;

delivering a liquid from a handle unit of the medical device to the vicinity of the lesion area through a distal opening portion of the guide wire lumen; and rotating the cutting portion via a drive shaft of the medical device to cut the lesion area into pieces.

10. The method according to claim 9, further comprising:

changing a position of the cutting portion in a circumferential direction by rotating an operation unit on the handle unit.

11. The method according to claim 9, further comprising:

changing a position of the cutting portion in a longitudinal direction by moving the handle unit or the extracorporeally exposed outer tube of the medical device and causing the outer tube to reciprocate along the longitudinal direction of the blood vessel.

12. The method according to claim 9, further comprising:

aspirating the saline solution liquid and the pieces cut from the lesion area via an aspiration lumen of the medical device.

13. The method according to claim 9, further comprising:

removing the medical device from the blood vessel.

14. A medical device for removing an object inside a biological lumen, comprising:

a rotatable drive shaft;

a cutting portion fixed to a distal portion of the drive shaft and configured to cut the object;

an outer tube configured to accommodate the drive shaft;

a handle unit, the handle unit configured to accommodate a proximal portion of the drive shaft and a proximal portion of the outer tube, the handle unit including an aspiration port configured to discharge a liquid outside of the handle unit, and the aspiration port configured to communicate with an aspiration lumen located between the outer tube and the drive shaft;

the drive shaft including a first wire rod helically wound around an axis of the drive shaft, and wherein the first wire rod is configured to directly face an inner peripheral surface of the outer tube;

wherein a helical winding direction of the first wire rod wound toward a proximal end direction of the drive shaft is a reverse direction of a rotational direction of the drive shaft;

the drive shaft includes a first drive shaft including the first wire rod and a second drive shaft including a second wire rod, and a distal end of the second drive shaft is located proximal to a proximal end of the first drive shaft, and the proximal end of the first drive shaft is interlocked with the distal end of the second drive shaft;

a winding direction of the second wire rod being a reverse direction of the winding direction of the first wire rod; and wherein the proximal end of the second drive shaft is spaced apart from the distal end of the first drive shaft, and the proximal end of the first drive shaft is interlocked with the distal end of the second drive shaft with a cylindrical tube, the cylindrical tube arranged on an outer peripheral surface of a proximal portion of the first drive shaft and an outer peripheral surface of a distal portion of the second drive shaft.

* * * * *